United States Patent
Won

(10) Patent No.: US 6,533,777 B2
(45) Date of Patent: Mar. 18, 2003

(54) MOXA CAUTERIZING DEVICE AND METHOD OF FORMING MOXA SINKER FOR THE CAUTERIZING DEVICE

(76) Inventor: Young-Doo Won, 134-16 Junggok-Dong, Kwangjin-Gu, Seoul 143-891 (KR)

(*) Notice: Subject to any disclaimer, the term of this patent is extended or adjusted under 35 U.S.C. 154(b) by 0 days.

(21) Appl. No.: 09/848,117

(22) Filed: May 2, 2001

(65) Prior Publication Data

US 2002/0165527 A1 Nov. 7, 2002

(51) Int. Cl.⁷ ............................................. A61B 18/04
(52) U.S. Cl. ........................................................ 606/27
(58) Field of Search .......................... 428/139; 606/44; 601/84, 15; 600/547, 548

(56) References Cited

U.S. PATENT DOCUMENTS 5,931,806 A    8/1999   Shimada .................... 604/24
6,083,591 A    7/2000   Yoo ......................... 428/40.1

*Primary Examiner*—Henry Bennett
*Assistant Examiner*—Sabrina Dagostino
(74) *Attorney, Agent, or Firm*—Lee & Hong

(57) ABSTRACT

The present invention relates to a moxa cauterizing device and a method of forming moxa sinkers for the cauterizing device which allow the treatment of palsy, cancerous cells or the like without causing burn on the skin of a patient by means of non-contacting method and allow the automatic and convenient forming of moxa sinkers.

Thus, the invention proposes a moxa cauterizing device comprising a moxa cauterizing can(1); a support(2) having magnetism; a magnet(3) mounted at a location of the outer circumference of the support(2); a moxa cauterizing plate(4) provided inside the moxa cauterizing can(1) in a vertically movable manner and formed with a plurality of ventilating holes(4a); and an elevation controlling means(5) connected to a connecting rod(4b) for raising and lowering the moxa cauterizing plate(4).

3 Claims, 9 Drawing Sheets

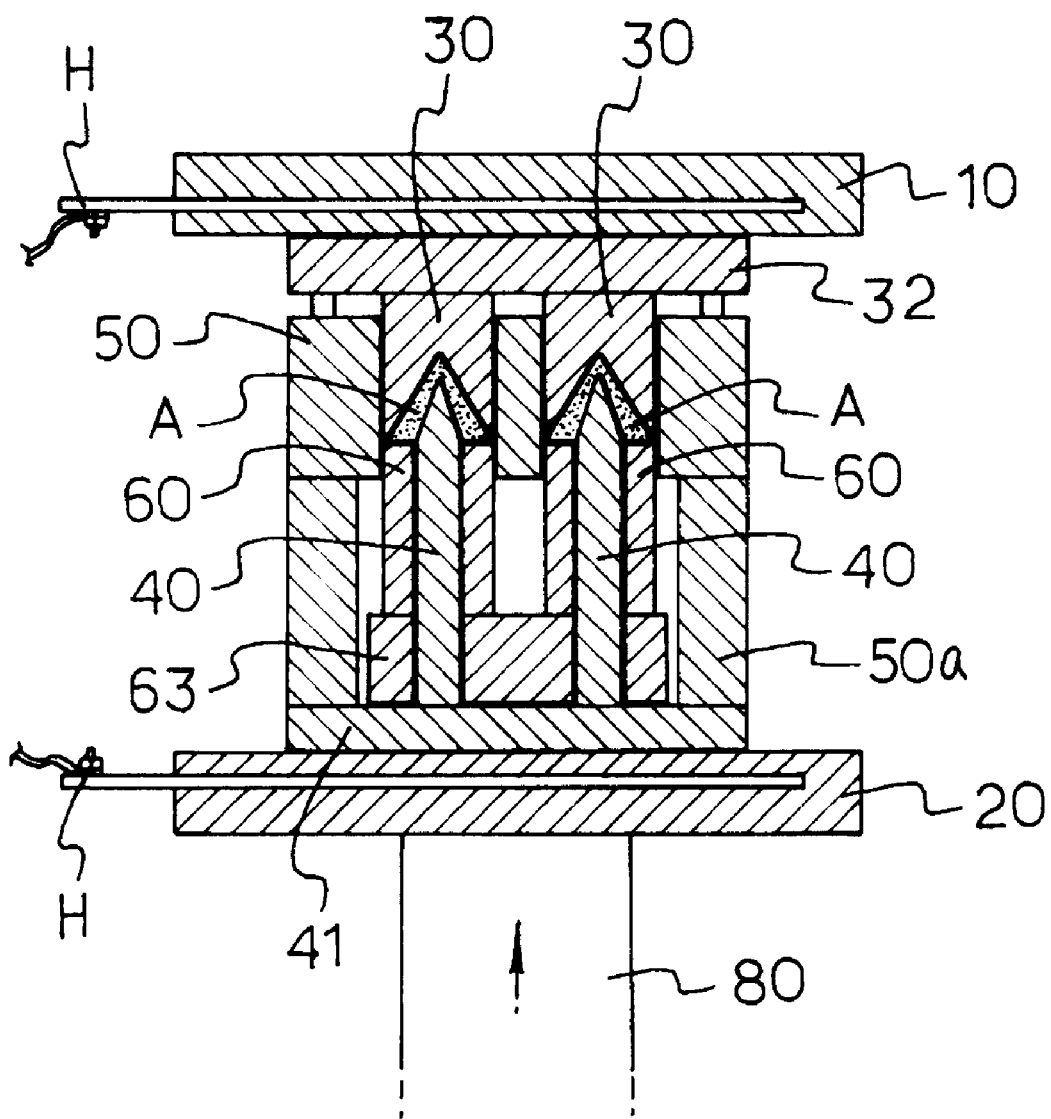

MOXA CAUTERIZING DEVICE AND METHOD OF FORMING MOXA SINKER FOR THE CAUTERIZING DEVICE

FIELD OF THE INVENTION

The present invention relates to a moxa cauterizing device and a method of forming moxa sinker for the cauterizing device which allow the treatment of palsy, cancerous cells or the like without causing burn on the skin of a patient through non-contacting method and allow the automatic and convenient forming of moxa sinkers.

BACKGROUND OF THE INVENTION

The far infrared rays which are electromagnetic waves with longer wave length than that of the visible rays, i.e. a wavelength of 4 to 1000 $\mu$m exhibits a heating effect. Those far infrared rays with wave length of 8 to 15 $\mu$m out of those far infrared rays are known to have excellent effects such as warming, neutralizing, circulating and ripening effect for living bodies. In contrast, the conventional physiotherapy was a treatment simply relying on vibration or magnetic flux.

In the conventional moxa cautery, moxa was brought into contact with the affected part of a patient, with result that various components contained in the moxa or wormwood were introduced in the body through the skin of the patient. This type of cauterizing method was disadvantageous because patients have to suffer from hot smoke and damaged skin due to the difficulty in controlling the temperature of the burning moxa.

Further, the conventional moxa cautery also has the problem that its therapeutic effect depends simply on the constituents included in wormwood or the strength of wormwood, as the treating method comprises merely contacting moxa directly on the affected parts of patients.

In addition, the moxa sinkers and the method for molding the sinkers had also problem in the conventional art. In the method, a rod is driven centrally deep into the heap of wormwood placed in a mold and subsequently the bulk wormwood was compacted or compressed manually to mold a moxa sinker. After turning the mold upside down, the rod is removed, so that the molded moxa usually in the form of a cone may result.

Because of the procedure as described above, the completed moxa has a central hole due to the use of a rod. When the moxa burns during cautery, the ingredient stream of wormwood may pass through the above-mentioned hole due to air convection phenomena to penetrate into the patient's body through skin pores.

In molding moxa sinkers according to the conventional technique, the molding operation was difficult and needed much time because it depended on tedious manual work. Molded products were easily broken due to weak compacting force. Further, when the compaction in molding the moxa sinker was incomplete, as was usual, generally the durability and medicinal effect of the moxa sinker are deteriorated.

SUMMARY OF THE INVENTION

The present invention was created to resolve the problems with the conventional art and the object of the invention is to provide a moxa cauterizing device which permits the improvement in the therapeutic effect by supplementing the effect of far infrared and magnetism to the basic efficacy of wormwood increased in spite of non-contacting application of moxa.

Another object of the invention is to provide a method for molding moxa sinks which permits a convenient and automatic molding of moxa sinks and which permits mass production of moxa sinks, burning longer, excellent in medicinal effect and resistant to breakage.

The above object is achieved according to an aspect of the invention by a cauterizing device comprising a moxa cauterizing can in the form of a cylinder, made of clay and coated with far infrared ray emitting ceramic films on the inner and outer surfaces; a support having magnetism, formed with a circular groove for detachably engaging with the underside of the moxa cauterizing can and formed with an inner bore for communicating with the inside of the moxa cauterizing can, the support being placed on an affected part of a patient in application; a magnet mounted at a location of the outer circumference of the support for forming a magnetic field; a moxa cauterizing plate provided inside the moxa cauterizing can in a vertically movable manner and formed with a plurality of ventilating holes, the moxa cauterizing plate receiving a moxa sinker on its top surface; and an elevation controlling means connected to the top end of a connecting rod for raising and lowering the moxa cauterizing plate, the connecting rod being vertically attached at a position of the perimeter of the moxa cauterizing plate.

The above object is also achieved according to another aspect of the invention by a method for molding moxa sinkers which comprises the steps of introducing respective 6 to 7 grams of dry wormwood with the age of over 3 years in the molding grooves of a die, and applying the heat for a temperature of 150 to 200° C. and a pressure of 110 to 120 kg/cm$^2$ for a period of 20 to 30 seconds, using the upper and lower molding punches, so that moxa sinkers each formed with a reverse V-formed groove and having a general form of cone and pyramid may be produced.

In the moxa cauterizer according to the invention, the energic stream including the component like cineol produced during the combustion of the leaves of wormwood with the period of growth of 3 or more years after germination, the far infrared rays from hot ceramic films and the magnetic field generated from the magnet mounted on the cauterizing device cooperate simultaneously in acting on the affected areas of a patient. Through this indirect influence on the affected areas or acupunctural spots, beside the normalization of abnormalized physical areas, various medical effects including the activation of tissue cells, and the increase in antitoxins, immune bacteriolysins etc. contained in the blood may be realized, so that physical disorders can be cured.

Further, those combined actions may help increase the red and white blood cells, and help form hemoglobin, opsonin calcium etc., so that the energy of body and spirit may be fortified and the fatigue and aging of physical constitution may be prevented.

The ingredients from wormwood and the like as described above may have advantageous effect in that various toxic or waste substances like alcohols, narcotics, heavy metals, agricultural chemicals taken in the human body may be gasified and discharged, or the residue may be decomposed and excreted as liquid, or still remaining solid mass will be converted to sticky pus and discharged outside the body.

Further, active components penetrate deep into the body to activate exothermic reaction to open clogged holes and increase the blood flow so as to increase the blood flow, so that thrombus, stroke and arteriosclerosis may be prevented. Moreover, activated hemoglobin increases the supply of oxygen and the removal of harmful matter, so that fatigue, neuralgia, rheumatism, sequelae of traffic accidents or the like can be treated with excellent result.

In addition, the activation of blood circulation and the promotion of metabolism contribute to the removal of excess subcutaneous fat for physical fitness and fair skin.

BRIEF DESCRIPTION OF THE DRAWINGS

FIG. 3 shows the perspective view of a moxa cauterizing plate, FIGS. 4 to 7 relates to one embodiment of a molding device for the purpose of illustrating the method for molding moxa sinks according to the invention, of which:

FIGS. 6a, 6b and 6c show side cross sections in the order of molding moxa sinks

DETAILED DESCRIPTION OF THE INVENTION

Preferred embodiments of the invention are described in detail in the following description in conjunction with the accompanying drawings.

Figure 1:
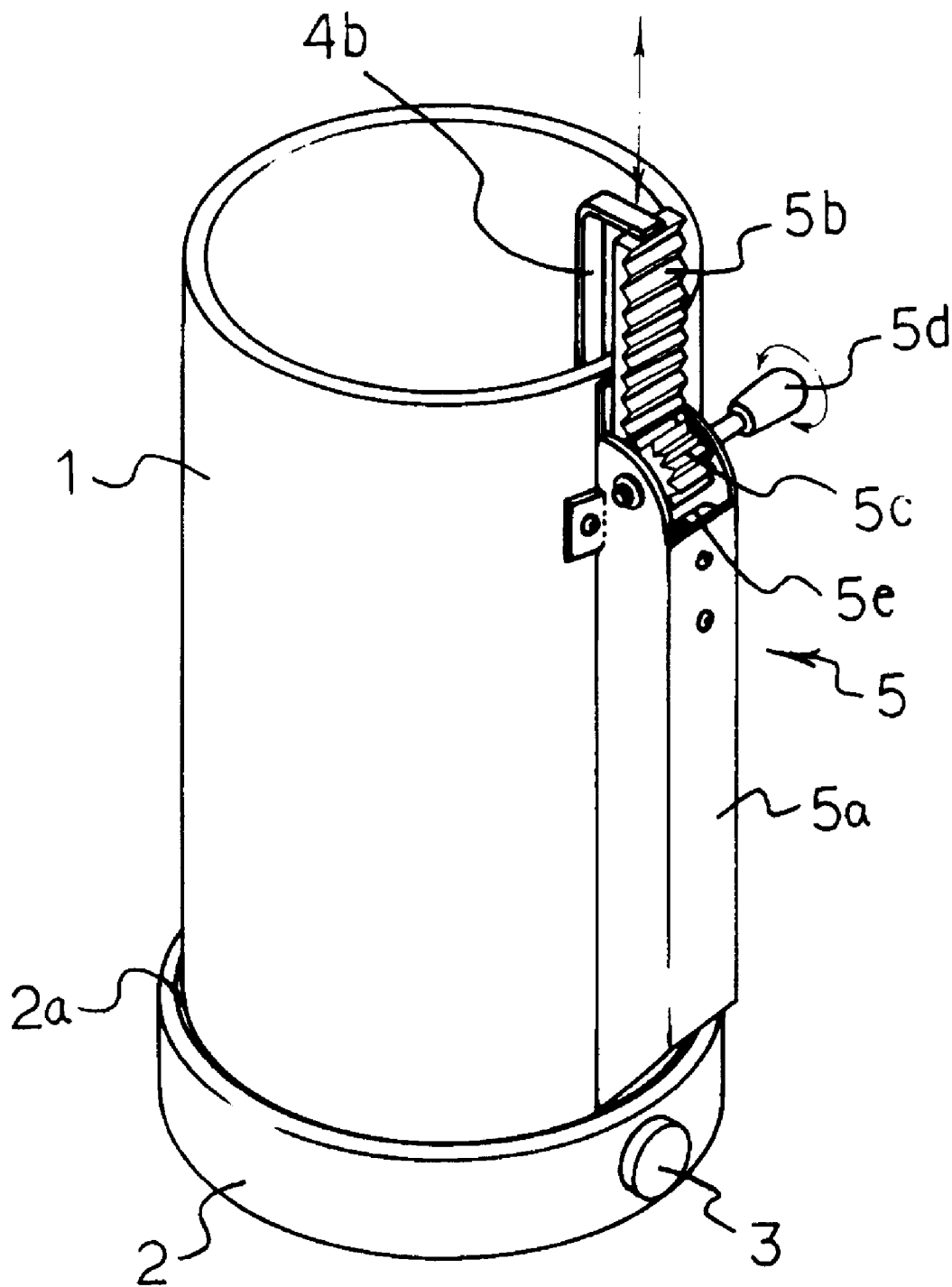
FIG. 1 shows the perspective view of a moxa sink cauterizing device according to an embodiment of the invention illustrating the construction of the device.
Figure 2:
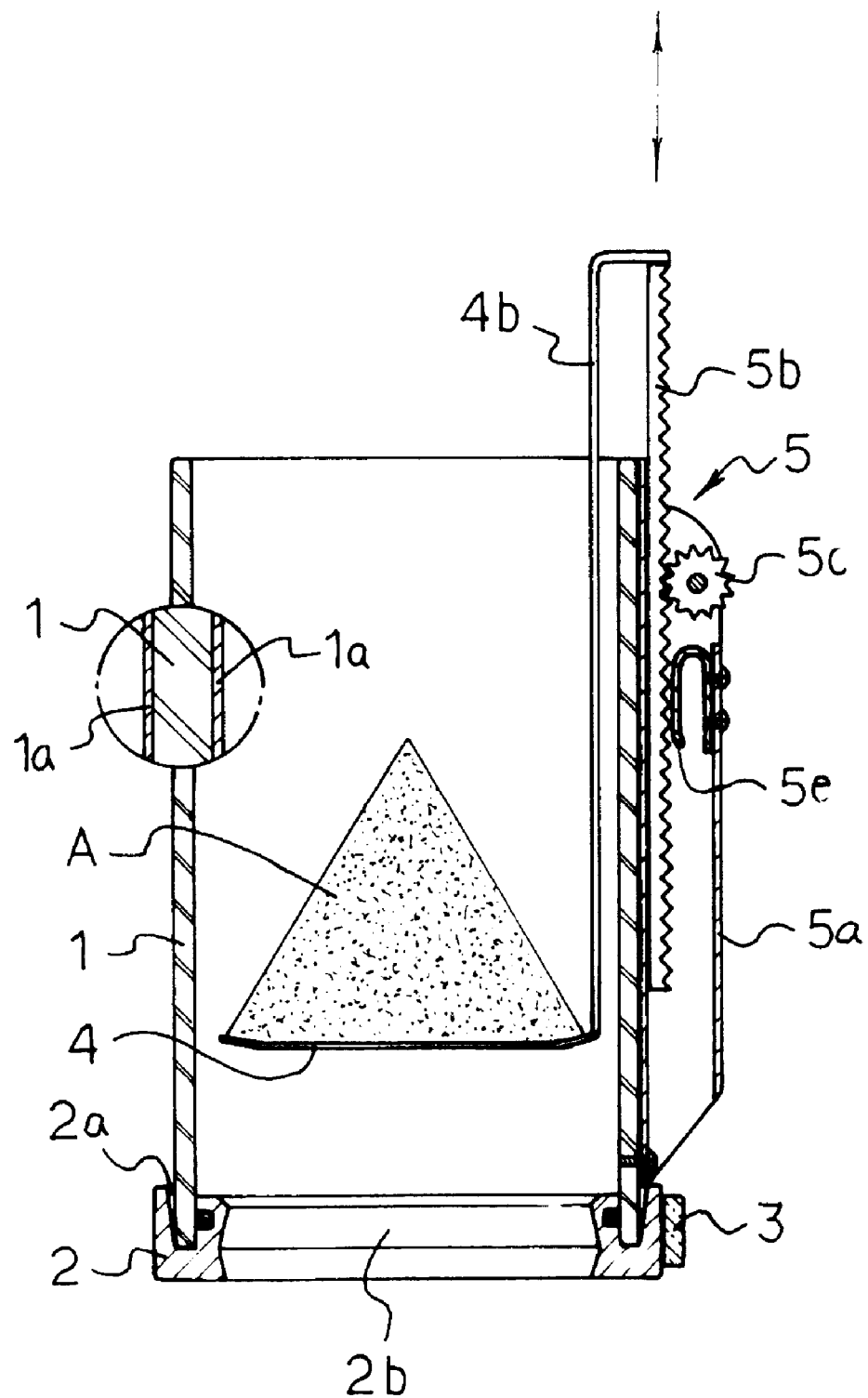
FIG. 2 shows the cross section of FIG. 1.
Figure 3:
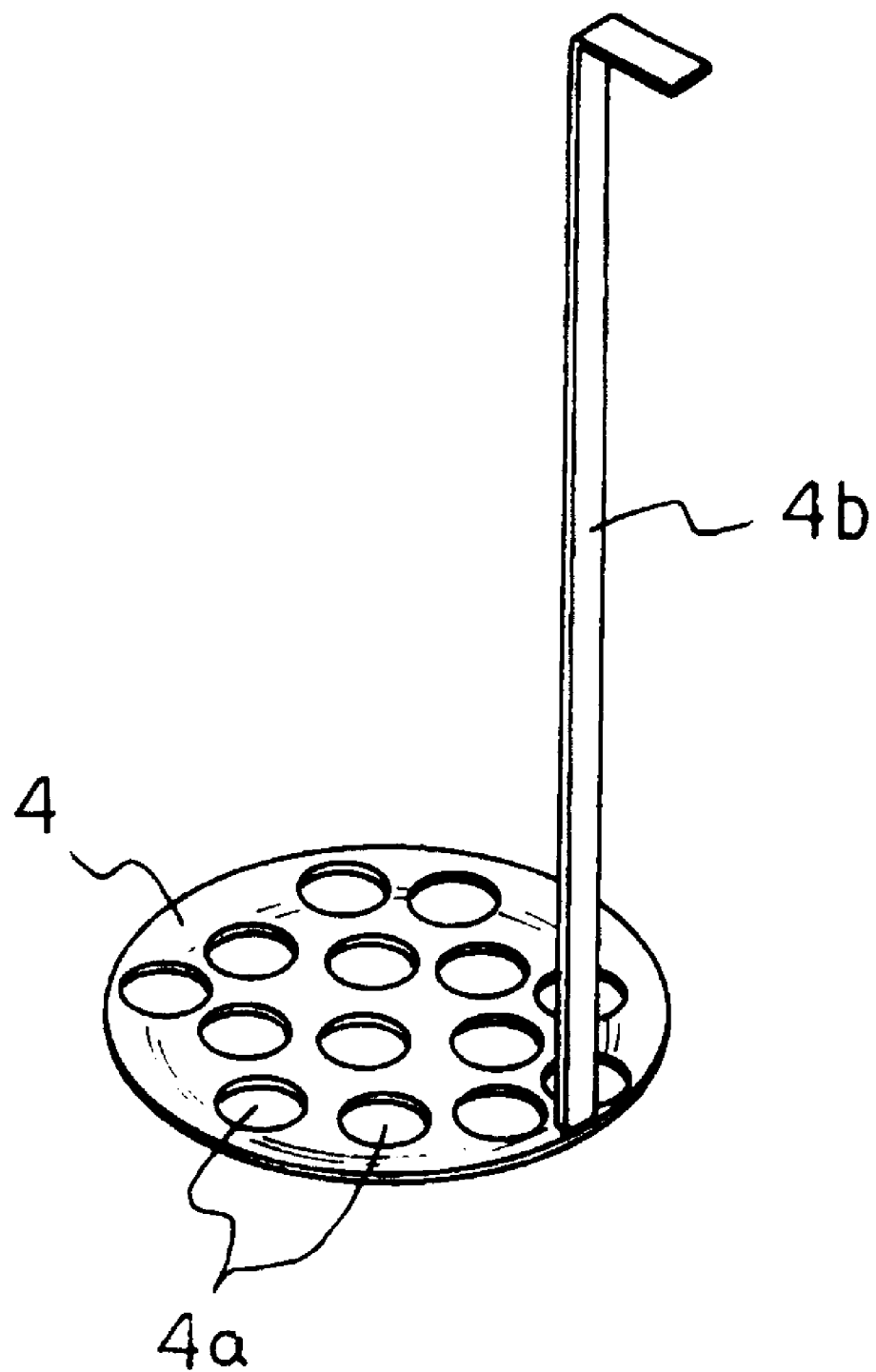

As seen in FIGS. 1 to 3, a moxa cauterizing device according to the invention includes a moxa cauterizing can 1 in the form of a cylinder, made of clay and coated with far infrared ray emitting ceramic films 1a on the inner and outer surfaces. A support 2 having a magnetism is formed with a circular groove 2a for detachably engaging with the underside of the moxa cauterizing can 1 and formed with an inner bore 2b for communicating with the inside of the moxa cauterizing can 1. The support is placed on an affected part of a patient in treatment. There is also included a magnet 3 mounted at a location of the outer circumference of the support 2 for forming a magnetic field. A moxa cauterizing plate 4 is provided inside the moxa cauterizing can 1 in a vertically movable manner and formed with a plurality of ventilating holes 4a. This moxa cauterizing plate receives a moxa sinker A on its top surface. And an elevation controlling means 5 connected to the top end of a connecting rod 4b is provided for raising and lowering the moxa cauterizing plate 4. The connecting rod 4b is vertically attached at a position of the perimeter of the moxa cauterizing plate 4.

The elevation controlling means 5 includes a guiding casing 5a which is provided on an area of the outer circumference of the moxa cauterizing can 1 and a rack 5b which is provided inside the guiding casing 5a in a vertically movable manner, the top end of the rack being connected to the top part of the connecting rod 4b. Also included is a pinion 5c which is provided rotatably in the top area of the guiding casing 5a for meshing with the rack 5b. A rotating knob 5d is connected to the rotation shaft of the pinion 5c to rotate the pinion 5c. And a supporting plate 5e is provided inside the guiding casing 5a for elastically supporting the rack 5b.

When rotating the rotating knob 5d, the pinion 5c integrally connected is rotated to move vertically the rack 5b in mesh with the pinion 5c, so that the elevation of the moxa cauterizing plate 4 can be controlled. A supporting plate 5e is elastically pressed against the rack 5b, whereby the rack 5b is prevented from dropping down due to its own weight.

The magnet 3, which is attached at one side of the support 2, is known to influence or improve the lines of magnetic force or its distribution around major acupunctural spots on human body to improve the blood circulation and relieve stiff muscles to thereby alleviate the feeling of physical fatigue, head ache, waist pain or the like, as demonstrated by some clinical tests.

The method of use and the effect of the moxa cauterizing device constructed as described above according to the invention are described below.

First, the moxa cauterizing can 1 is placed on the affected area of a patient such that the support 2 connected with the bottom of the can 1 may be positioned on the center of the affected area and a moxa sinker with e.g. the triangular cross section is disposed on the moxa cauterizing plate 4. Subsequently, when the moxa A is burnt, the smoke and fume generating from the moxa, including cineol, sesquiterpene, calcium chloride, alkali sulfate and the like are spread within the moxa cauterizing can 1, penetrating the affected skin, for the period of about 30 minutes based on one affected area, wherein the indirect cauterizing can take about the same effect as the direct cauterizing.

When a patient feels hot due to the heat generated from a burning moxa sinker A, the cauterizing plate 4 is caused to move up to alleviate the hotness by using the elevation controlling means 5 mounted on the moxa cauterizing can 1. On the other hand, when the moxa sinker A is almost burnt and produces little heat, the cauterizing plate 4 is lowered to approach the patient's skin by using the elevation controlling means 5 to intensify the influence.

Further, the support 2 connected to the bottom part of the moxa cauterizing can is magnetized to produce magnetic flux by the magnet 3 attached to the side of the support 2.

At the same time, the far infrared rays are emitted from the ceramic films 1a coated on the inner and outer surfaces of the moxa cauterizer 1 to influence the affected areas of the patient. As described, the wormwood constituents from the burning moxa, far infrared rays from ceramic coatings 1a and the magnetic flux generated by the magnet 3 are penetrated into the body through or near the affected parts to activate exothermic reaction among others, so that plugged bodily holes may be opened, and the blood vessels may be expanded to increase the blood flow.

Generally, moxa cauterizing is conducted with regard to basic three affected areas in order to treat a patient, wherein for one affected area, preferably the cauterizing as described above is conducted three times, with the duration of about 30 minutes. Deviating from this basic formula, the application sites, period and frequency may be appropriately adjusted depending on the condition of the patients' health and disease.

Now, a method for molding moxa sinkers according to the invention, to be used for the moxa cauterizing device according to the invention will be described.

Referring to FIGS. 4 to 7, which shows a preferred embodiment of a device for molding moxa sinkers according to the invention, the molding device is seen to comprise punch and die holders 10 and 20 disposed in the upper and lower location of a main body B, each of the punch and die holders being provided with a heater H; upper punches 30 disposed under the punch holder 10 and provided each with a moxa sinker molding groove 31 having the form of cone or pyramid; lower punches 40 disposed above the die holder 20 and each having a pointed top end; a die 50 formed with molding openings 51, the molding openings being disposed above the lower punches 40 and suited for receiving the upper punches 30; knock out 60 slidable vertically between the die 50 and the lower punches 40 and suited to be fitted in the molding openings 51, the knock out being formed with punch holes 61 for receiving the lower punches 40; chains 70 fixed at opposite sides of the upper punches 30, the lower ends of the chains being detachably fixed at connection pins 62 of the knock out 60; a piston 80 for vertically moving the die holder 20; a motor 90 for supplying hydraulic pressure to the piston 80; and a controller 100 for controlling pressure, temperature and time.

Figure 4:
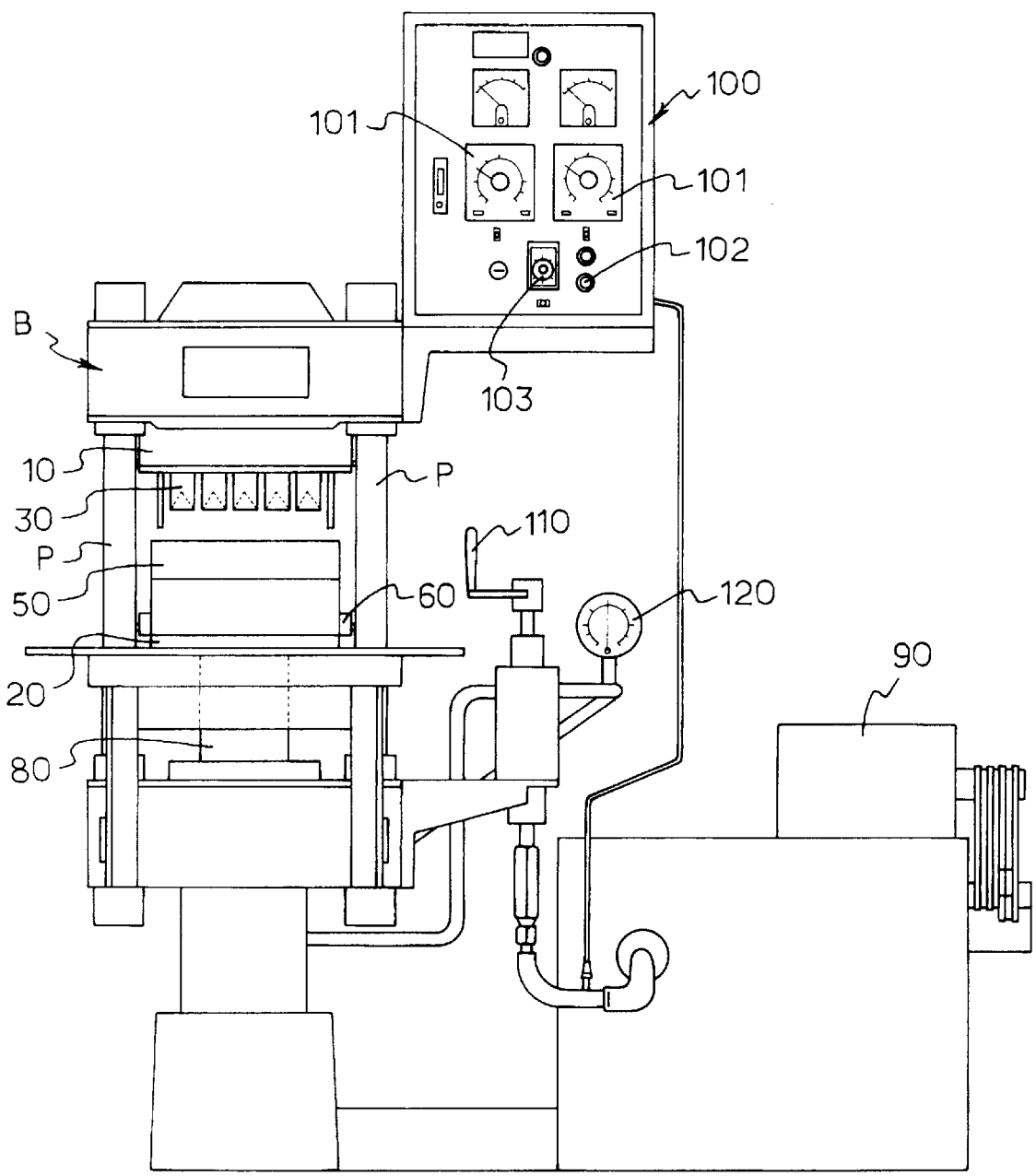
FIG. 4 shows the overall arrangement view.

Here, the upper and lower parts of the main body B are connected by guiding posts P, as seen in FIG. 4.

The heaters H which are pre-built in each of the punch and die holders 10 and 20 function to heat the upper and lower punches 30 and 40, the die 50 and the knock out 60 at around 150 to 200° C.

Figure 5:
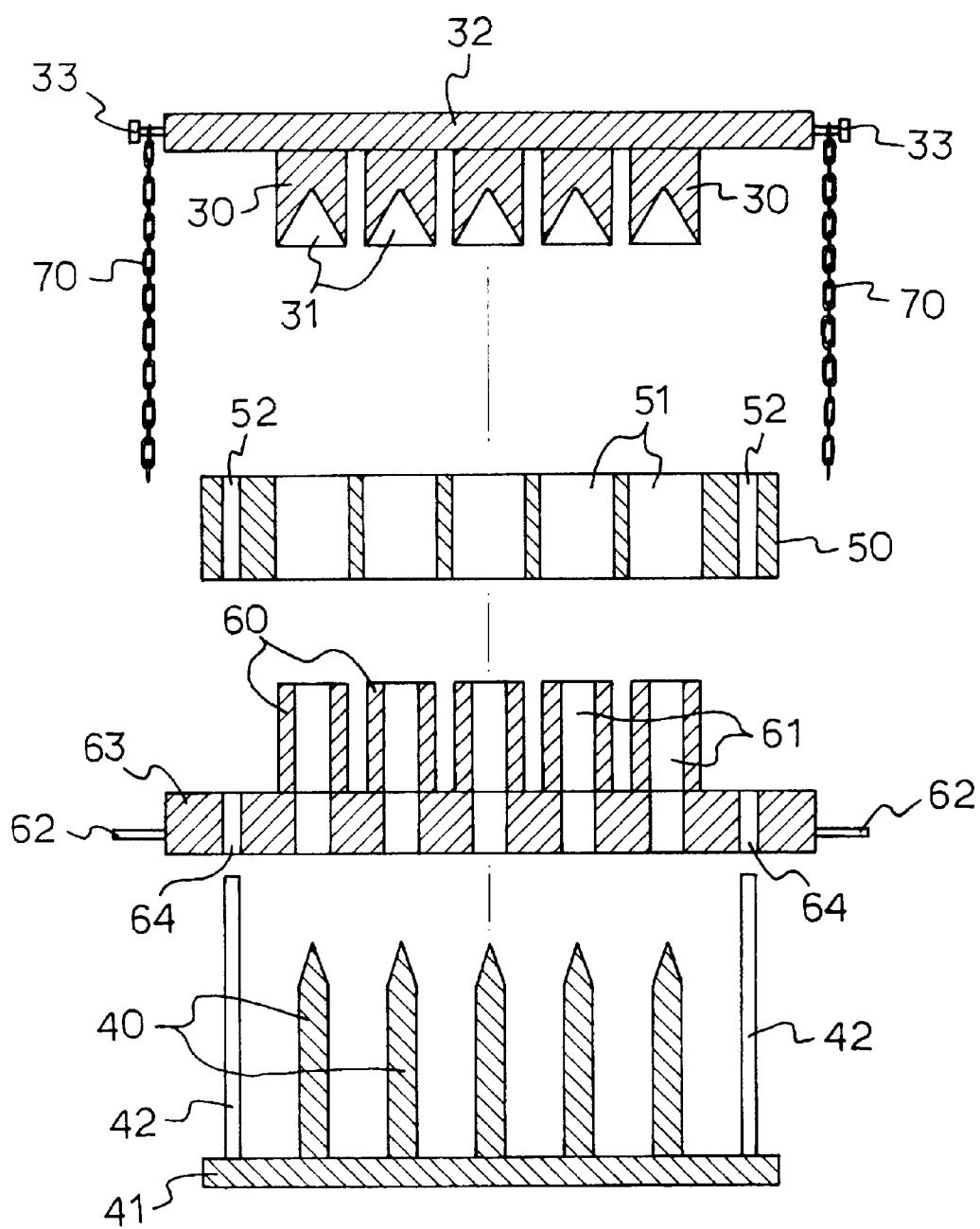
FIG. 5 shows the exploded cross section for essential parts.

The plate 32 is provided with a plurality of upper punches 30 at a finite interval. And the plate 32 has, at opposite sides, fixing pins 33 for fixing the upper ends of the chains 70, as shown in FIG. 5.

On the bottom plate 41, there are arranged, in a fixed manner, a plurality of long lower punches 40 at a regular interval so as to correspond to the upper punches 30. Also on the bottom plate 41, guide pins 42 are disposed on both terminal sides, as seen in FIG. 5. Further, on the front and rear sides of the bottom plate 41, die fixing pieces 50*a* are anchored, as seen in FIGS. 6 and 7.

The die 50 is fixedly disposed on the die fixing pieces 50*a*, wherein a space for knockout is provided between the front and rear fixing pieces 50*a*. The die 50 is formed with a plurality of molding openings 51 facing to the upper punches 30. Accordingly, the die 50 is moved up or down, integrally with the lower punches 40.

The plate 63 is provided with a number of knockouts 60 at a finite interval facing to the molding openings 51 and the plate has, at its terminal sides, connection pins 62 for fixing the lower ends of the chains 70.

The die 50 and knockout plate 63 are formed at both sides with pin holes 52 and 64 for receiving guide pins 42.

The piston, which functions to move hydraulically the die holder 20 up or down, is raised with a hydraulic supply when the motor 90 is driven, and is lowered when a pressure relieving switch 110 is operated, in which switch a pressure meter 120 is incorporated.

The controller 100 includes thermometers 101, operating switch 102, timer 103 and the like. The operation of the motor 90 is controlled by the timer 103.

The method for molding moxa sinkers comprises the steps of introducing respective 6 to 7 grams of dry wormwood with the age of over 3 years in the molding grooves 51 of a die 50, and applying the heat for a temperature of 150 to 200° C. and a pressure of 110 to 120 kg/cm$^2$ for a period of 20 to 30 seconds, using the upper and lower molding punches 30 and 40, so that moxa sinkers A each formed with a reverse V-formed groove A1 and having a general form of cone and pyramid may be produced.

Specifically, the moxa sinkers A are molded according to the process of the invention including the following steps.

Figure 6A:
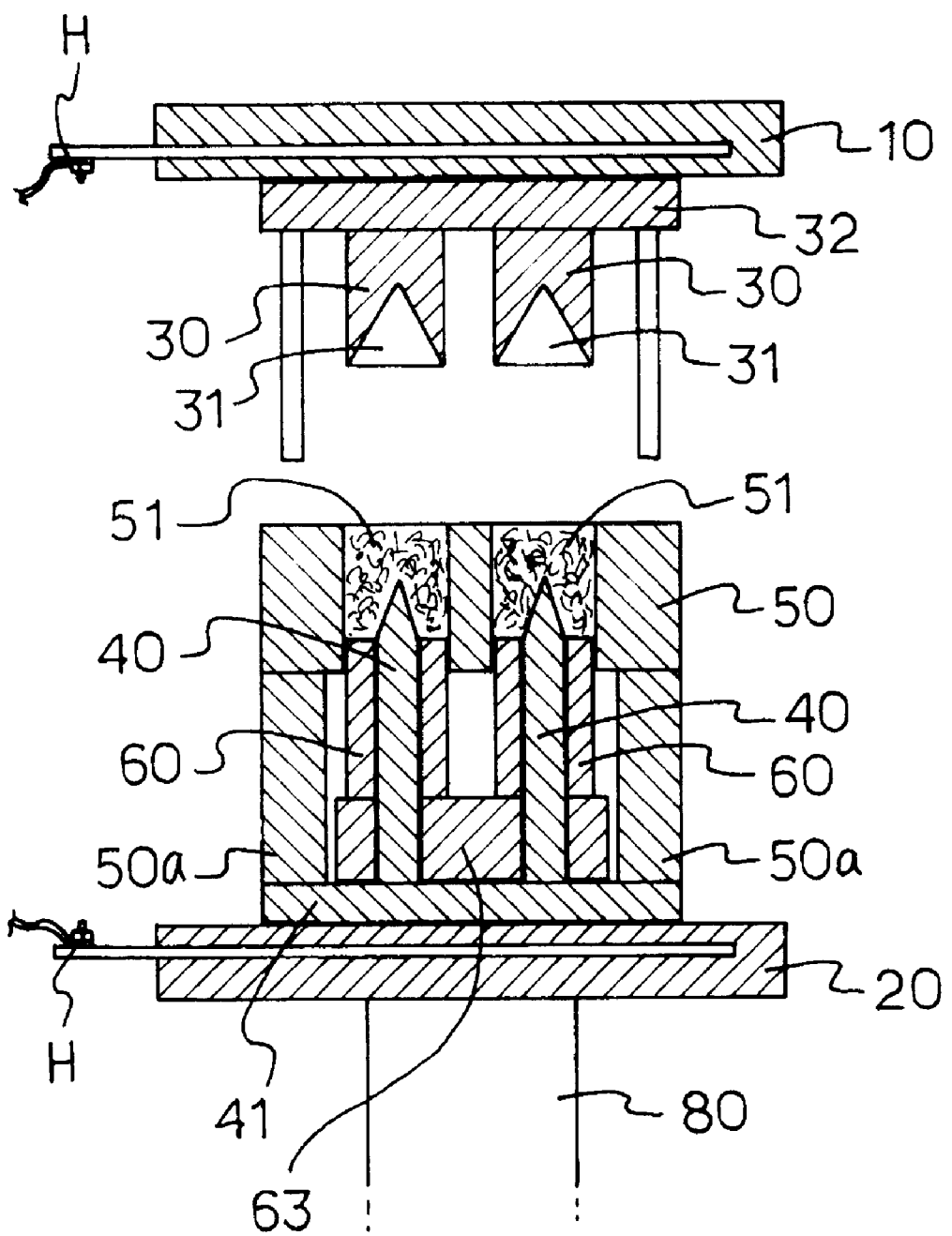
Figure 7:
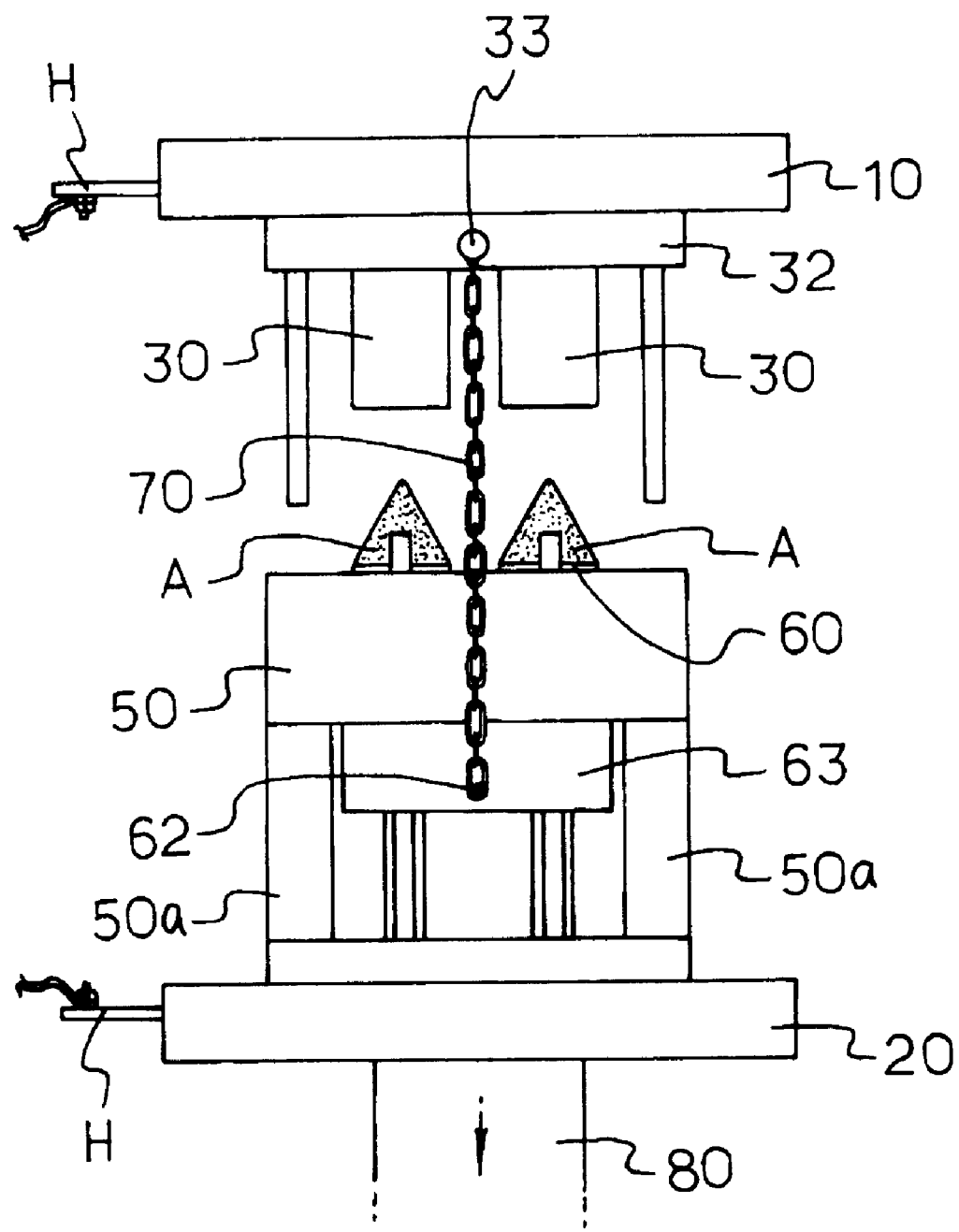
FIG. 7 shows the side view of the state corresponding to FIG. 6c.

First, with the piston 80 lowered as in FIG. 6*a*, dry wormwood aged over 3 years and weighing 6 to 7 grams based on one moxa sinker is packed in molding grooves 51 of the molding die 50 and then the piston 80 is caused to move up through the actuation of the motor 90 by turning the operating switch 102 on. When die holder 20 is elevated, as shown in FIG. 6*b*, the moxa filled in the openings 51 is entrapped between the conical tips of lower punches 40 and the molding grooves 31 of upper punches 30 to yield dense moxa sinkers A, after the molding openings 51 of the die 50 have approached the respective corresponding upper punches 30. At this time, the upper and lower punches 30 and 40, the die 50 and the knockout 60 are heated at a temperature of 150 to 200° C. by heaters H, the piston 80 is acted upon by a pressure of 110 to 120 kg/cm$^2$ and a period of 20 to 30 seconds are set in the timer 103.

Specifically, with the die holder 20 elevated as seen in FIG. 6*b*, with regard to the molding openings 51 of the die 50, the upper punches 30 each formed with a moxa sinker molding groove 31 in the form of a cone or pyramid are pressed from the upside and the knockout 60 together with the lower punches 40 are positioned in from the downside. Therefore, the wormwood filled in the molding grooves 51 is compressed and formed into cone- or pyramid-formed moxa sinkers A due to heat and pressure. The finished moxa sinkers are each formed with a conical depression A1 due to the lower punches 40.

Subsequently, when the molding is completed following the operation of the motor 90 for the period as set by the timer 103, a buzzer makes a sound. Then, the lower ends of the chains 70 are caused to be tied with the connection pins 62 of the knockout 60 and the die 50 together with lower punches 40 are caused to move down, allowing the knockout 60 to fall only as much as permitted by the tightening chains 70, by actuating the pressure relieving switch 110 to relieve the piston 80 from hydraulic pressure, as seen in FIG. 6*c*.

Figure 6C:
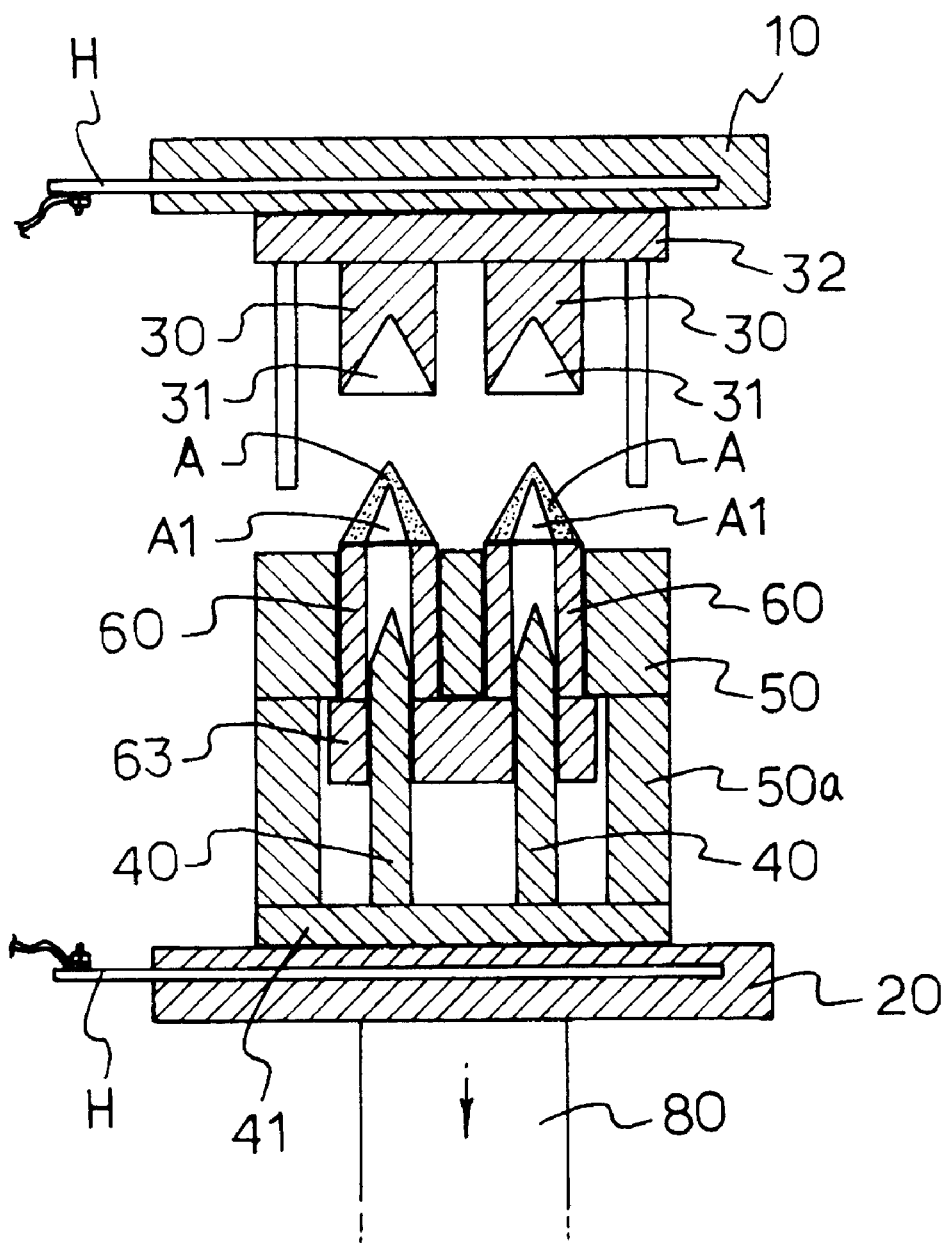

That is, as the knockout and plate 60 and 63 are tied to the chains 70, as seen in FIG. 7, only the die and lower punches 50 and 40 are lowered, leaving the knockout at the suspended position as seen in FIG. 6*c*. The molded moxa sinkers A are now ready to be recovered, as they are protruded upward from the die 50 with the help of the knockout 60.

In conducting the next molding operation after the recovery of products moxa sinkers A, the piston 80 is moved up somewhat to facilitate the disconnection of the chains 70 by loosening them. After disconnecting the chains 70 from the connection pins 62, the assembly including the die 50 and the knockout assembly are fully lowered to be in the state as seen in FIG. 6*a*, so that the same molding procedure as in the first operation can start with filling dry wormwood in molding openings 51.

Therefore, according to the present invention, the moxa sinkers which are hard, firm and durable and have excellent medicinal effect can be produced at a large scale in an automatic manner.

It is to be understood that, while the invention was described mainly with respect to specific embodiments, the invention is never restricted to those embodiments and a variety of modifications and alterations would be possible to a man skilled in the art by referring to the description or drawings presented here and within the spirit of the invention and thus those modifications or alterations are to fall within the scope of the invention, which scope should be limited only by the attached claim.

What is claimed is:

1. A moxa cauterizing device comprising a moxa cauterizing can(1) in the form of a cylinder, made of clay and coated with far infrared ray emitting ceramic films(1*a*) on the inner and outer surfaces; a support(2) having a magnetism, formed with a circular groove(2*a*) for detachably engaging with the underside of the moxa cauterizing can(1) and formed with an inner bore(2*b*) for communicating with the inside of the moxa cauterizing can(1), the support being placed on an affected part of a patient in application; a magnet(3) mounted at a location of the outer circumference of the support(2) for forming a magnetic field; a moxa cauterizing plate(4) provided inside the moxa cauterizing can(1) in a vertically movable manner and formed with a plurality of ventilating holes(4*a*), the moxa cauterizing plate receiving a moxa sinker A on its top surface; and an elevation controlling means(5) connected to the top end of a connecting rod(4*b*) for raising and lowering the moxa cauterizing plate(4), the connecting rod being vertically attached at a position of the perimeter of the moxa cauterizing plate.

2. The moxa cauterizing device according to claim 1, wherein the elevation controlling means(5) comprises a guiding casing(5*a*) provided on an area of the outer circumference of the moxa cauterizing can(1); a rack(5*b*) provided inside the guiding casing(5*a*) in a vertically movable manner, the top end of the rack being connected to the top part of the connecting rod(4*b*); a pinion(5*c*) provided rotatably in the top area of the guiding casing(5*a*) for meshing with the rack(5*b*); a rotating knob(5*d*) connected to the rotation shaft of the pinion(5*c*), for rotating the pinion(5*c*); and a supporting plate(5*e*) provided inside the guiding casing(5*a*), for elastically supporting the rack(5*b*).

3. The moxa cauterizing device according to claim 1, wherein the moxa sinker (A) received on top surface of the moxa cauterizing plate (4) is formed with a reverse V-formed groove (A1) and into a general form of a cone and pyramid.

* * * * *